(12) United States Patent
Rabouille

(10) Patent No.: US 8,758,805 B2
(45) Date of Patent: Jun. 24, 2014

(54) SKIN MOISTURIZING COMPOSITIONS

(75) Inventor: Thierry Rabouille, Alby sur Cheran (FR)

(73) Assignee: Galderma Research & Development, Biot (FR)

( * ) Notice: Subject to any disclaimer, the term of this patent is extended or adjusted under 35 U.S.C. 154(b) by 85 days.

(21) Appl. No.: 12/591,715

(22) Filed: Nov. 30, 2009

(65) Prior Publication Data

US 2010/0143446 A1  Jun. 10, 2010

Related U.S. Application Data

(63) Continuation of application No. PCT/EP2008/056722, filed on May 30, 2008.

(60) Provisional application No. 61/006,290, filed on Jan. 4, 2008, provisional application No. 60/924,827, filed on Jun. 1, 2007.

(51) Int. Cl.
*A61Q 19/00* (2006.01)

(52) U.S. Cl.
USPC .......................................... 424/443; 424/401

(58) Field of Classification Search
None
See application file for complete search history.

(56) References Cited

U.S. PATENT DOCUMENTS

| | | | |
|---|---|---|---|
| 2004/0005340 A1* | 1/2004 | Patel et al. | 424/401 |
| 2005/0100565 A9* | 5/2005 | Patel et al. | 424/401 |
| 2005/0100592 A1* | 5/2005 | Zulli et al. | 424/450 |
| 2005/0271595 A1* | 12/2005 | Brown | 424/10.1 |
| 2006/0147397 A1* | 7/2006 | Uehara et al. | 424/62 |
| 2006/0182708 A1* | 8/2006 | Bockmuhl et al. | 424/74 |
| 2006/0286050 A1* | 12/2006 | Yu et al. | 424/63 |
| 2007/0003511 A1* | 1/2007 | Schulz et al. | 424/74 |
| 2008/0069898 A1* | 3/2008 | Smith et al. | 424/642 |
| 2009/0117061 A1* | 5/2009 | Gross | 424/59 |

FOREIGN PATENT DOCUMENTS

FR  2868952  10/2005

OTHER PUBLICATIONS

International Search Report in English, for corresponding PCT/EP2008/056722, dated Jan. 5, 2009.
Extended Search Report issued on Jun. 18, 2012, by the European Patent Office in corresponding European Patent Application No. 12163543.

* cited by examiner

*Primary Examiner* — Robert A Wax
*Assistant Examiner* — Olga V Tcherkasskaya
(74) *Attorney, Agent, or Firm* — Dentons US LLP

(57) ABSTRACT

Novel skin moisturizing compositions are applied onto dry skin, particularly mild to moderately dry skin, are non-irritating and contain at least one natural moisturizing factor, *butyrospermum parkii*, at least one silicone, and Panthenol.

10 Claims, 3 Drawing Sheets

*$P \leq .05$;

*$P \le .05$;

SKIN MOISTURIZING COMPOSITIONS

CROSS-REFERENCE TO EARLIER APPLICATIONS

This application is a continuation of PCT/EP2008/056722, filed May 30, 2008 and designating the United States (published in the English language on Dec. 4, 2008 as WO 2008/145747 A2), which claims benefit of U.S. Provisional Applications Nos. 60/924,827, filed Jun. 1, 2007 and 61/006,290, filed Jan. 4, 2008, each hereby expressly incorporated by reference in its entirety and each assigned to the assignee hereof.

BACKGROUND OF THE INVENTION

1. Technical Field of the Invention

The present invention relates to novel moisturizing compositions and application thereof onto dry skin and particularly mild to moderate dry skin.

2. Description of Background and/or Related and/or Prior Art

Many dermatologists maintain that good skin care is an important part of any treatment regimen and also important in maintaining good dermatological health.[1-4] Since patients with skin disorders often also have damaged skin barrier functions, dermatologists will typically prescribe a gentle skin care regimen in addition to their treatment regimen to prevent further damage and perhaps, restore the skin barrier function.[2,3,5] The gentleness of a family of skin products (Galderma Laboratories) has been the primary reason why many physicians trust these products for their patients.[1,6,7] Very few products have been added to this line due to the strict requirement that all members of the line maintain the high standards of appropriateness for use in dermatology patients.

SUMMARY OF THE INVENTION

The present invention provides novel moisturizers (designated: CDA). Thus, it has now surprisingly been found that the moisturizing compositions according to the invention have a favorable and improved effect with regards to the hydration properties and the irritation potential of moisturizing compositions in the form of lotions (hereinafter CDA) in humans with mild to moderate dry skin in comparison to other recommended products that are currently available. In addition, CDA had better hydration at 2 hours after application when compared to the other test lotions and was significantly different from the untreated control at all time points out to 24 hours.

The present invention thus features moisturizing compositions comprising, formulated into a pharmaceutically acceptable medium, at least one natural moisturizing factor (NMF), butyrospermum parkii (shea butter), at least one silicone, and Panthenol. Preferably, the silicone is selected from cyclomethicone, dimethiconol or a mixture thereof and more preferably selected from the list of cyclopentasiloxane, cyclohexacyclosiloxane, dimethiconol or a mixture thereof.

In a preferred embodiment of the invention, the natural moisturizing factor is a mixture of ingredients and comprising sodium PCA (pyrrolidone carboxylic acid). Preferably, the mixture comprises at least 10% of sodium PCA.

In another embodiment, the invention provides a moisturizing composition comprising the following ingredients:
water,
glycerin,
butyrospermum parkii (shea butter),
cyclopentasiloxane,
sodium PCA,
Panthenol,
dimethiconol, and
optionally, sodium Polyacrylate.

More particularly, the said moisturizing composition comprises the following ingredients in concentrations expressed by weight with regards to the total weight of the composition:
from 50% to 85%, preferably from 55% to 70% of water,
from 1% to 20%, preferably from 10% to 19% of glycerin,
from 1% to 10%, preferably from 1% to 5% of butyrospermum parkii (shea butter),
from 0.1% to 3%, preferably from 0.5% to 2% of cyclopentasiloxane,
from 0.1% to 5%, preferably from 0.5% to 3% of sodium PCA,
from 0.1% to 5%, preferably from 0.1% to 2% of Panthenol,
from 0.05% to 3%, preferably from 0.05% to 1% of dimethiconol, and
optionally, from 0.01% to 2%, preferably from 0.1% to 1% of sodium polyacrylate.

The said moisturizing compositions may comprise at least one of the following ingredients in concentrations expressed by weight with regards to the total weight of the composition:
fatty components,
emulsion stabilizer,
preservative,
emulsifying agent and/or
pH adjuster.

According to the present invention, the said moisturizing compositions are in a form of emulsion such as cream, lotion, gel, impregnated towels, patch, washing product such as body wash, face wash.

Another aspect of the invention is the application of the moisturizing compositions as described above for hydrating or moisturizing a skin in need. CDA provides hydration as early as 2 hours after application. In a preferred embodiment, the skin in need is dry skin and preferably a mild to moderate dry skin.

Another aspect of the invention is a regime or regimen for hydrating or moisturizing a skin in need comprising administering a composition as described above on the skin surface. In one embodiment, the skin in need is a human skin.

In a preferred embodiment, the skin in need is dry skin and preferably a mild to moderate dry skin. Many dermatologists maintain that good skin care is an important part of any treatment regimen and also important in maintaining good dermatological health. The gentleness of a family of products (Galderma Laboratories) has been a hallmark over several decades and is the primary reason why many physicians trust these products for their patients with compromised skin. Very few products have been added to this line due to the strict requirement that all members of the line maintain the high standards of appropriateness for use in dermatology patients. The present invention provides a new moisturizer/moisturizing composition (designated: CDA). As described in the examples to follow, studies demonstrating the favorable effect of the moisturizing composition according to the invention were conducted to analyze the hydration properties of this moisturizer in comparison to four of the other recommended products that are currently available. Over a 24-hour period, CDA consistently performed as the top moisturizer at all time points as determined objectively by corneometry. In addition, the new moisturizer was the only tested product to effect significantly better hydration in as early as 2 hours after application. Furthermore, the coreometric hydration analysis was repeated in subjects with very dry skin, where CDA was found to add significant hydration to the skin. In addition, a 14-day cumulative irritation potential study was conducted to compare the gentleness of CDA to other products that are currently recommended. White petrolatum and sodium lauryl sulfate were also included as negative and positive controls, respectively. CDA had a cumulative score of 0.00 which was lower than petrolatum (cumulative score 1.9). The results of these studies show that this newest moisturizer in this family of skin care products is hydrating and gentle and expands the choices available to dermatologists and their patients. The intercellular matrix is the skin's first line of defense against water loss. When the lipid and NMF content of skin is reduced, one experiences surface roughness, flaking, fine lines, and a tight, uncomfortable feeling.

A first aspect of the present invention is a moisturizing composition comprising, in a pharmaceutically acceptable medium, at least one natural moisturizing factor, *butyrospermum parkii* (shea butter), at least one silicone and Panthenol. Preferably, the silicone is selected from the list of cyclomethicone, dimethiconol or a mixture thereof and more preferably selected from cyclopentasiloxane, cyclohexacyclosiloxane, dimethiconol or a mixture thereof. In a preferred embodiment of the invention, the natural moisturizing factor is a mixture of ingredients and comprises sodium PCA. Preferably, the mixture comprises at least 10% of sodium PCA. Indeed, natural moisturizing factors (NMFs) make up an expansive group of ingredients that include amino acids, ceramides, hyaluronic acid, cholesterol, fatty acids, triglycerides, phospholipids, glycosphingolipids, urea, linoleic acid, glycosaminoglycans, mucopolysaccharide, and sodium PCA (pyrrolidone carboxylic acid).

All of the skin's supporting NMFs and lipids are present in the intercellular structure of the epidermis, both from skin cells and in the lipid content on the surface of skin. When any of these ingredients are used in skin-care products, they appear to help stabilize and maintain this complex intercellular-skin matrix. Although none of these very good NMFs and lipids can permanently affect or change skin, they are great at temporarily keeping depleted skin from feeling dry and uncomfortable. More importantly, all of these ingredients, and many more, can help support the intercellular area of the skin by keeping it intact. This support helps prevent surface irritation from penetrating deeper into the skin, works to keep bacteria out, and aids the skin's immune/healing system. Selecting moisturizers of any kind with NMFs (whether they are labeled as being anti-aging, anti-wrinkle, serums, lotions, or sunscreens) allows the skin to do its job of repairing and regenerating itself without the impedances brought on when skin is suffering from dryness and excess irritation (Sources: *Clinical Geriatric Medicine*, February 2002, pages 103-120; *Progressive Lipid Research*, January 2003, pages 1-36; *Journal of the European Academy of Dermatology and Venereology*, November 2002, pages 587-594; *Contact Dermatitis*, June 2002, pages 331-338; *Journal of Investigative Dermatology*, May 1996, pages 1096-1101; *British Journal of Dermatology*, November 1995, pages 679-685; *Skin Pharmacology and Physiology*, September-October 2004, pages 207-213; *Free Radical Research*, April 2002, pages 471-477; and *Journal of Lipid Research*, May 2002, pages 794-804).

Another aspect of the present invention is a moisturizing composition as defined above which comprises, in a pharmaceutically acceptable medium, at least a complex of specific ingredients (designated: ERC or Epidermal Replenishing Complex) that comprises at least one natural moisturizing factor. The preferred natural moisturizing factor is sodium PCA In the context of the invention, the ERC is a mixture of ingredients and comprises at least 10% of sodium PCA (Natural Moisturizing factor) or other NMFs. More particularly, ERC comprises the following ingredients:
*butyrospermum parkii* (shea butter),
cyclopentasiloxane,
sodium PCA as natural moisturizing factor,
dimethiconol,
panthenol.

Therefore, one embodiment of the invention is an "EPIDERMAL REPLENISHING COMPLEX" (hereinafter ERC) which comprises select active ingredients that provide the skin with the essential components required for its good balance:
Sodium PCA,
Shea Butter,
Panthenol,
Dimethiconol,
Cyclopentasiloxane.

Cyclopentasiloxane is one of the many types of silicones. In general, silicones are known for their ability to lubricate, waterproof and provide shine.

Dimethiconol is derived from silica; it provides a non-greasy lubricant for hair conditioners, and adds shine to hair. In addition, the ERC strengthens actions of other skin conditioning agents presents in CDA selected from the following ingredients:
Glycerin,
Macadamia Oil,
Hydrogenated Polyisobutene,
Vitamin E Acetate.

Thanks to its very efficient complex of specific ingredients, the "EPIDERMAL REPLENISHING COMPLEX" (ERC), that works in synergy with the other components of the formula, the CDA allows the dry skin to recover its essential functions and healthy aspect. CDA was demonstrated able to restore then improve moisture level and reinforce the skin barrier function (Example 2).

In one embodiment, the present invention provides a moisturizing composition comprising the following ingredients:
water,
glycerin,
*butyrospermum parkii* (shea butter),
cyclopentasiloxane,
sodium PCA (natural moisturizing factor),
Panthenol,
dimethiconol, and
optionally, sodium polyacrylate.

More particularly, the said moisturizing composition comprises the following ingredients in concentration expressed by weight with regards to the total weight of the composition:
50% to 85%, preferably from 55% to 70% of water,
1% to 20%, preferably from 10% to 19% of glycerin,
1% to 10%, preferably from 1% to 5% of *butyrospermum parkii* (shea butter),
0.1% to 3%, preferably from 0.5% to 2% of cyclopentasiloxane,
0.1% to 5%, preferably from 0.5% to 3% of sodium PCA,
0.1% to 5%, preferably from 0.1% to 2% of Panthenol,
0.05% to 3%, preferably from 0.05% to 1% of dimethiconol,
0.5% to 2.5%, preferably from 1% to 2% of ceteareth 20,
optionally, 0.01% to 2% preferably from 0.1% to 1% of sodium polyacrylate.

The said moisturizing composition may additionally comprise at least one of the following ingredients in concentration expressed by weight with regards to the total weight of the composition:

fatty components,
emulsion stabilizer,
preservative,
emulsifying agent and/or
pH adjuster.

According to the present invention, fatty components means, any mineral oil, vegetable oil, animal or synthetic oil, fatty acid, fatty alcohol, synthetic polymer or esters, silicone oil or ester alone or in a mixture. One example of mineral oil is paraffin oil with different viscosity such as Primol 352®, Marcol 82®, Marcol 152® sold by Esso company.

As vegetable oil, exemplary is any oil extract from vegetables such as macadamia ternifolia nut oil, soy oil, maize oil, sunflower oil, sweet almond oil, palm oil, sesame oil. Examples of animal oil are lanolin, squalene, fish oil, mink oil and its squalane derivative called Cosbiol marketed by the Laserson company.

As synthetic oil, exemplary are the esters such as cetearyl isononanoate (known as Cetiol SN PH® by company Cognis France), isopropyl palmitate (known as Crodamol IPP® by Croda company), diisopropyl adipate (known as Crodamol DA by Croda company), caprylic/capric triglyceride such as product known as Miglyol 812® sold be the company Huls/Univar.

As volatile or non-volatile silicone oil, exemplary are dimethicones such as those marketed under the trademark Q7-9120 silicone fluid with viscosity 20 cst to 12,500 cst or the product ST-Cyclomethicone-5 NF® marketed by Dow Corning. Examples of synthetic polymers or esters are polymers such as Polyisobutene and Hydrogenated Polyisobutene. In a preferred embodiment, Hydrogenated Polyisobutene is a polymer with branched chains aliphatic hydrocarbon structure, devoid of ring structure.

Fatty acids and fatty alcohols are well known by one skilled in the art and will be selected accordingly.

Examples of emulsion stabilizer are, but not limited to the list of the following ingredients:
Carbomer and its salts,
Acrylates/C10-30 Alkyl Acrylate Crosspolymer,
Hydroxyethylcellulose,
HydroxypropylCellulose,
Polyacrylamide family (simulgel 600, Sepigel 305, Sepigel 501),
Xanthan gum.

A preferred embodiment of the invention includes an Acrylates/C10-30 Alkyl Acrylate Crosspolymer.

Examples of preservatives are benzalkonium chloride, bronopol, chlorhexidine, chlorocresol and its derivatives, ethylic alcohol, phenethylic alcohol, potassium sorbate, diazolidinylurea, benzylic alcohol, parabens alone or in mixture.

Exemplary emulsifying agents include lecithin, beeswax or any other natural wax, Emulsifying Wax NF, Cetearyl Alcohol/Ceteareth 20, Glyceryl Stearate, Polysorbate 20, Ceteareth 20, ethoxylated glyceryl monostearate, cetearyl alcohol and sodium stearoyl lactylate alone or in a mixture. Preferably, Ceteareth 20 and cetearyl alcohol are selected, alone or mixed.

Exemplary pH adjusters are typical mineral or organic base or acid pH neutralizing agents such as triethanolamine, solution of sodium hydroxide at 10%, succinic acid/sodium succinate buffer, citric acid/sodium citrate buffer.

One skilled in the art will select one of these complementary ingredients and/or the concentration thereof such that the advantageous properties of the composition are not or substantially not altered.

Most of these complementary ingredients can be incorporated in a composition of the invention in a range of concentrations from 0.001 to 20% with regards to the total weight of the composition:

In a specific embodiment, the present invention provides a moisturizing composition comprising the following ingredients:
water,
glycerin,
synthetic polymers or esters such as hydrogenate polyisobutene,
cetearyl alcohol,
ceteareth 20,
fatty component such as macadamia ternifolia nut oil,
*butyrospermum parkii* (shea butter),
tocopherylacetate,
cyclopentasiloxane,
sodium PCA (natural moisturizing factor),
dimethiconol,
Panthenol,
optionally phenoxyethanol,
optionally, sodium polyacrylate,
optionally stearoxytrimethylsilane,
optionally stearic alcohol,
optionally, preservative such as benzyl alcohol,
optionally, farnesol,
optionally, emulsion stabilizer such as acrylate/C10-30 alkylacrylate crosspolymer,
optionally, pH adjuster such as Sodium hydroxide,
optionally, pH adjuster such as Citric acid.

In a preferred embodiment, the moisturizing composition comprises more particularly the following ingredients in concentrations expressed by weight with regards to the total weight of the composition:
50% to 85%, preferably from 55% to 70% of water,
1% to 20%, preferably from 10% to 19% of glycerin,
1% to 10%, preferably from 1% to 5% of *butyrospermum parkii* (shea butter),
0.1% to 3%, preferably from 0.5% to 2% of cyclopentasiloxane,
0.1% to 5%, preferably from 0.5% to 3% of sodium PCA,
0.1% to 5%, preferably from 0.1% to 2% of Panthenol,
0.05% to 3%, preferably from 0.05% to 1% of dimethiconol
optionally, 0.01% to 2%, preferably from 0.1% to 1% of sodium polyacrylate,
1% to 7%, preferably from 4% to 6% of synthetic polymers or esters and preferentially hydrogenated polyisobutene,
optionally, 2% to 5%, preferably from 3% to 4% of cetearyl alcohol,
0.5% to 2.5%, preferably from 1% to 2% of ceteareth 20,
optionally, from 1% to 10% preferably from 3% to 4% of fatty component preferentially macadamia ternifolia nut oil,
0.1% to 0.3%, preferably from 0.5% to 1.5% of tocopherylacetate benzyl alcohol,
0.05% to 0.5% of stearoxytrimethylsilane,
0.01% to 0.5% of stearic alcohol,
optionally, 0.01% to 0.5 of farnesol,
optionally, 0.01% to 0.5% of emulsion stabilizer, preferentially acrylate/C10-30 alkylacrylate crosspolymer,
optionally, sodium hydroxide, qsp pH 6 to 7,
optionally, citric acid, qsp pH 6 to 7.

According to the present invention, the moisturizing compositions are in different forms. These compositions can be in the form of an emulsion such as cream, lotion, gel, impregnated towels, patch, cleansing product such as body wash, face wash or any other appropriate form. The present invention also provides that the moisturizing composition have hydrating and less irritating effect on the skin. As described in example 2, the present invention provides compositions for the treatment of mild to moderate dry skins. As shown also in the examples, CDA provides better hydration as early as 2 hours after application when compared to the other test lotions and was significantly different from the untreated control at all time points out to 24 hours. The present compositions of the invention can be applied onto irritated and dry skins. The irritation might be due to aggressive factors, natural or chemical factors such as medicaments, wind, sea water. Therefore, in one specific embodiment, the invention provides the application of the moisturizing composition as a medicament for the treatment of dry and/or irritated skin.

Therefore, another embodiment of the invention is a regime or regimen for hydrating or moisturizing a skin in need comprising administering a subject composition onto the skin surface. In a preferred embodiment, the skin in consideration is a dry skin and preferably mild to moderate dry skin. Preferentially, the skin is a human skin. By human skin it is understood any human skin such as adult, child or baby skin.

All test products had significantly improved skin scaling when compared to the untreated control at 2, 4, 8, 12, and 24 hours after application. Comparisons of the test products and untreated control were made using analysis of variance (ANOVA) with pair-wise comparison's (Fisher's LSD).

Figure 2:
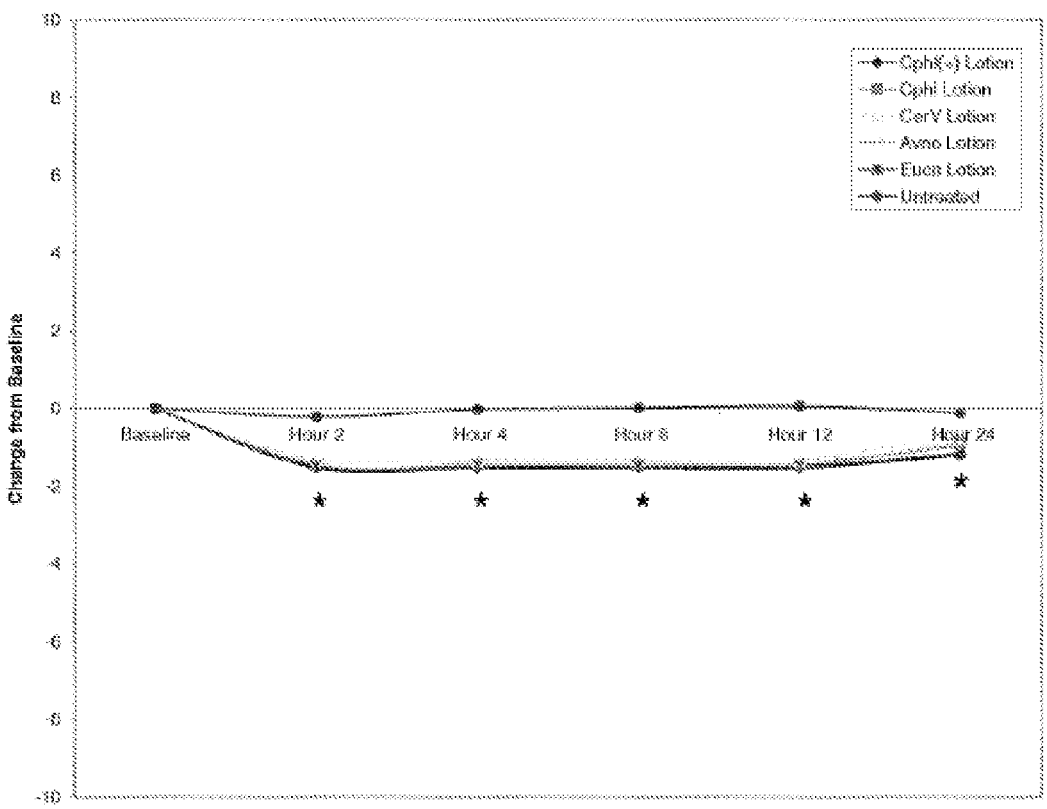

FIG. 2. Improved Skin Cracking over 24 Hours All test products had significantly improved skin cracking when compared to the untreated control at 2, 4, 8, 12, and 24 hours after application. Comparisons of the test products and untreated control were made using analysis of variance (ANOVA) with pair-wise comparison's (Fisher's LSD).

Figure 3:
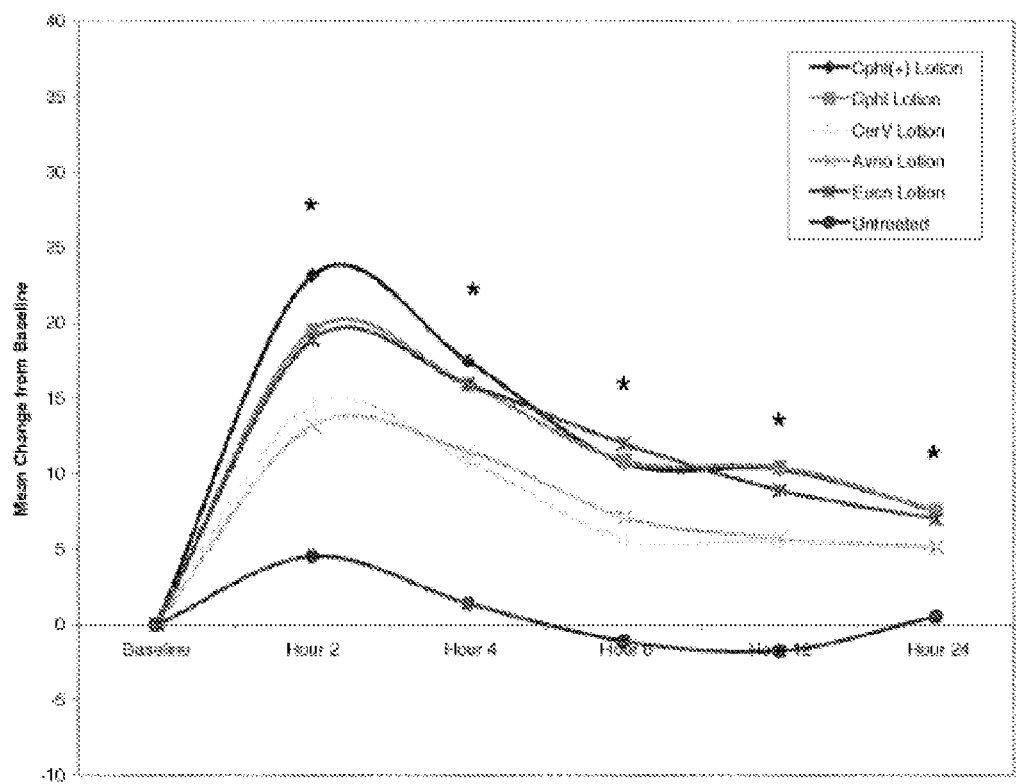

FIG. 3. Hydration Measurements by Corneometry Over 24 Hours

All test products had significantly improved skin hydration when compared to the untreated control at 2, 4, 8, 12, and 24 hours after application, while CDA lotion (mentioned Cphl (+)) had the highest measurement of hydration at 2 and 4 hours. Comparisons of the test products and untreated control were made using analysis of variance (ANOVA) with pair-wise comparison's (Fisher's LSD).

TABLE

Table 1. Standardized Cumulative Irritation Scores and Classification

In order to further illustrate the present invention and the advantages thereof, the following specific examples are given, it being understood that same are intended only as illustrative and in nowise limitative. In said examples to follow, all parts and percentages are given by weight, unless otherwise indicated.

EXAMPLE 1

Compositions

This example illustrates several compositions with detailed ingredients:

|  | Composition A | Composition B |
|---|---|---|
| Cetearyl Alcohol | 2.8 | 4.2 |
| Ceteareth 20 | 1.2 | 1.8 |
| Shea Butter | 1 | 3 |
| Acrylate/C1-30 Alkyl Acrylate Crosspolymer | 0.01 | 0.05 |
| Sodium Polyacrylate | 0.10 | 0.05 |
| Dimethiconol | 0.08 | 0.15 |
| Phenoxyethanol | 0.25 | 0.90 |
| Hydrogenated Polyisobutene | 4.00 | 6.00 |
| Macadamia Oil | 1.50 | 3 |
| Panthenol | 0.20 | 0.30 |
| Cyclopentasiloxane | 1 | 1.42 |
| Sodium PCA | 1.00 | 1.50 |
| Glycerin | 15 | 18 |
| Tocopheryl Acetate | 1.00 | 1.00 |

EXAMPLE 2

Studies to analyze the hydration properties and the irritation potential of moisturizing composition CDA in the form of lotions in volunteers with mild to moderate dry skin for comparison to other recommended products that are currently available.

A two day, single-blinded controlled clinical study was conducted to assess the ability of CDA lotion to deliver moisture to the skin after a single application. Evaluations of skin moisture content were made by the Corneometer® (CM 825, Courage+Khazaka, Germany) and in addition to a clinical visual grading of skin scaling and cracking. Patients, ages 18 to 65-years with mild to moderate dry skin on the lateral aspect of the lower legs, were eligible for enrollment. They also had to be willing to not wet, shave, or apply any additional products to the test area during the two day clinical visits. Individuals with uncontrolled diseases (i.e., diabetes, hypertension, hyperthyroidism, and/or hypothyroidism) and/or any disease or condition of the skin (i.e., active psoriasis, active eczema, tattoos, scarring, cuts/scrapes/scratches, sunburn, etc.) in the test area were excluded from the study. Clinical measurements included clinical grading and Corneometer® measurements prior to product application, and again at 2, 4, 8, 12 and 24 hours after application. The Corneometer® quantified moisture content in the stratum corneum (SC) by an electrical capacitance method. This measurement employs arbitrary units that increase as the skin becomes more hydrated. CDA lotion was compared to other currently marketed moisturizers designated as follows: Cphl lotion (Galderma Laboratories, L. P.), CerV lotion (Coria Laboratories, Ltd.), Avno lotion (Johnson & Johnson Consumer Companies, Inc.), and Eucn lotion (Beiersdorf, Inc.). Skin scaling and cracking were evaluated based on a 5-point scale where 0=none and 4=obvious large scales (>1.0 mm) or obvious cracking/fissuring in the skin. Comparisons of the test products and untreated control were made using analysis of variance (ANOVA) with pair-wise comparison's (Fisher's LSD).

In addition, a 14-day cumulative irritation potential study was conducted to compare the gentleness of CDA lotion to other products according to published methods.[8,9] Male or female patients ages 18 to 70-years, with Fitzpatrick skin types I-IV, and who were willing to avoid direct sun exposure of the test area and avoid the use of tanning beds for the duration of the study were eligible for enrollment. Patients with active psoriasis, active allergic skin responses, active eczema, or sunburn, acne, abrasions, scar tissue, tattoos, and/or a skin disease at the test site, or those who are using anticancer, immunosuppressive treatments/medications, and/or radiation, or use of topical steroids or other drugs at the test site were excluded from the study. The predictive patch test technique was used to compare CDA lotion to Cphl lotion, CerV lotion, Avno lotion, and Eucn lotion. Occlusive patches with 100 micro liters of test product were applied to the skin daily for 14 days. Patches with sodium lauryl sulfate, 1.0% was used as a positive control while white petrolatum was used as a negative control.

All adverse events were reported in terms of severity and relatedness to study product during both studies.

Figure 1:
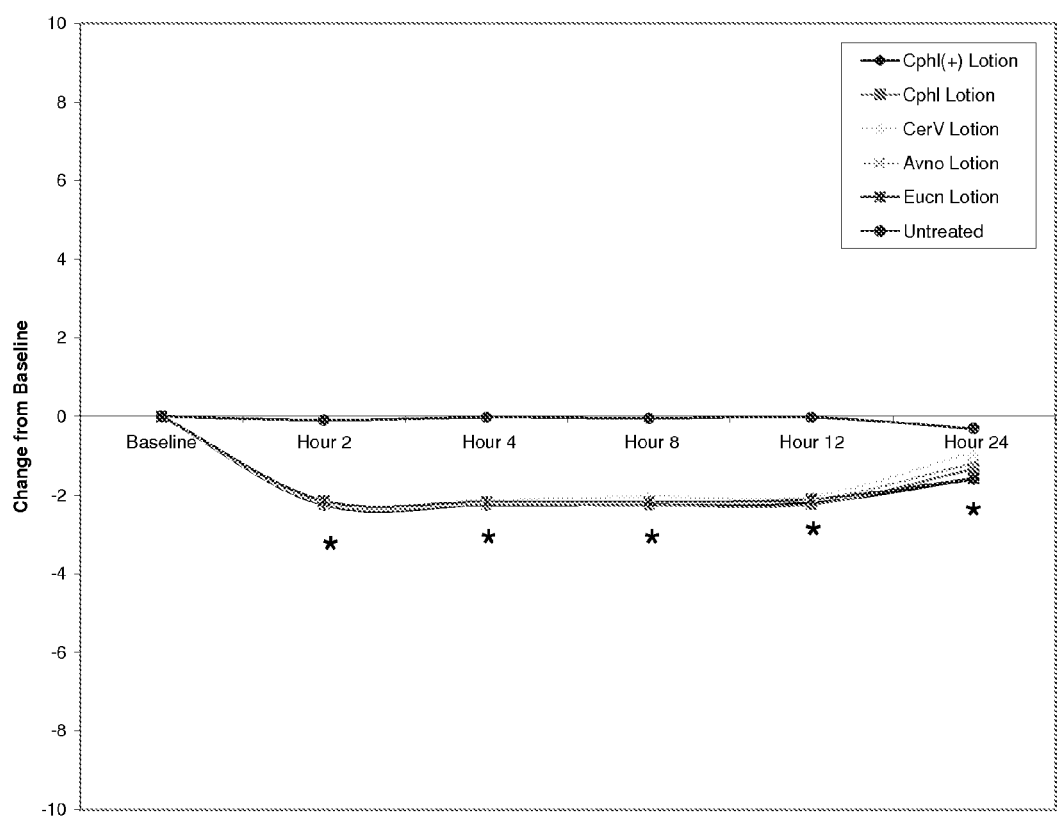
FIG. 1. Improved Skin Scaling over 24 Hours

Results:

ANOVA comparisons indicated that all test products had significantly improved skin scaling (FIG. 1) and skin cracking (FIG. 2) when compared to the untreated control at 2, 4, 8, 12, and 24 hours after application ($P \leq 0.05$). ANOVA comparisons also indicated that all test products were significantly more hydrating at all time points when compared to the untreated control as determined by Corneometer® measurements ($P \leq 0.05$; FIG. 3). In addition, CDA lotion had the highest measurement of hydration in as early as 2 hours after application. Even 4 hours after application, CDA lotion had better hydration than the other test lotions. CDA lotion, Cphl lotion, and Eucn lotion provided the most hydration out to 24 hours when compared to the other lotions.

Results from a 14-day cumulative irritation potential study revealed the gentleness of CDA lotion in comparison to other test products that are currently recommended. CDA lotion had a cumulative irritation score of 0.00 which was lower than the negative control, white petrolatum (cumulative score 1.9). Sodium lauryl sulfate 1.0%, the positive control, had a cumulative irritation score of 595.4 (Table 1). According to the irritation classification used by Berger and Bowman, all test products were classified as a "mild material" (category I) while the positive control was classified as "possibly mild" (category III) based on standardized cumulative irritation scores.

No adverse events were reported over the course of these studies.

TABLE 1

| Test Material | Standardized Cumulative Score | Category | Classification[a] |
|---|---|---|---|
| CDA lotion | 0.0 | I | Mild material - experimental irritation |
| Cetaphil lotion | 0.0 | I | Mild material - experimental irritation |
| Avno lotion | 0.0 | I | Mild material - experimental irritation |
| Cerv lotion | 1.9 | I | Mild material - experimental irritation |
| Eucn lotion | 21.3 | I | Mild material - experimental irritation |
| Negative Control White Petrolatum | 1.9 | I | Mild material - experimental irritation |
| Positive Control - Sodium lauryl sulfate, 1.0% | 595.4 | III | Possibly mild in normal use |

[a] Irritation classification according to the method of Berger and Bowman[89]

CONCLUSIONS

CDA lotion had better hydration at 2 hours after application when compared to the other test lotions and was significantly different from the untreated control at all time points out to 24 hours ($P \leq 0.05$).

CDA lotion was reported to be gentle based on the standardized cumulative irritation score of zero.

CDA lotion expands the choices of mild skin moisturizers available to dermatologists and their patients.

Each patent, patent application, publication, text and literature article/report cited or indicated herein is hereby expressly incorporated by reference in its entirety.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

REFERENCES

1. Laquieze S, Czernielewski J and Baltas E. Beneficial use of cetaphil moisturizing cream as part of a daily skin care regimen for individuals with rosacea. *J Dermatolog Treat* 2007; 18(3): 158-162.
2. Laquieze S, Czernielewski J and Rueda M J. Beneficial effect of a moisturizing cream as adjunctive treatment to oral isotretinoin or topical tretinoin in the management of acne. *J Drugs Dermatol* 2006; 5(10):985-990.
3. Subramanyan K. Role of mild cleansing in the management of patient skin. *Dermatol Ther* 2004; 17 Suppl 1:26-34.
4. Bikowski J. The use of cleansers as therapeutic concomitants in various dermatologic disorders. *Cutis* 2001; 68(5 Suppl):12-19.
5. Bouwstra J A and Ponec M. The skin barrier in healthy and diseased state. *Biochim Biophys Acta* 2006; 1758(12): 2080-2095.
6. Draelos Z D. The effect of cetaphil gentle skin cleanser on the skin barrier of patients with rosacea. *Cutis* 2006; 77(4 Suppl):27-33.
7. Ananthapadmanabhan K P, Moore D J, Subramanyan K, et al. Cleansing without compromise: The impact of cleansers on the skin barrier and the technology of mild cleansing. *Dermatol Ther* 2004; 17 Suppl 1:16-25.
8. Bowman J P, Berger R S, Mills O H, et al. The 21-day human cumulative irritation test can be reduced to 14 days without loss of sensitivity. *J Cosmet Sci* 2003; 54(5):443-449.
9. Berger R S and Bowman J P. A reappraisal of the 21-day cumulative irritation test in man. *J Toxicol—Cut & Ocular Toxicol* 1982; 1 (2):109-115.

What is claimed is:

1. A moisturizing composition, wherein the composition comprises the following ingredients in a concentration expressed by weight with regard to the total weight of the composition:
from 50% to 85% of water,
from 1% to 20% of glycerin,
from 1% to 10% of *butyrospermum parkii*,
from 0.1% to 3% of cyclopentasiloxane,
from 0.1% to 5% sodium pyrrolidone carboxylic acid,
from 0.1% to 5% of Panthenol,
from 0.05% to 3% of dimethiconol, and
optionally, from 0.01% to 2% of sodium polyacrylate.

2. The moisturizing composition as defined by claim 1, wherein the composition additionally comprises at least one of the following ingredients in a concentration expressed by weight with regard to the total weight of the composition:
- from 1% to 10% fatty components,
- from 0.01% to 0.5% emulsion stabilizer, and/or
- from 0.1% to 0.3% preservative, and
- optionally pH adjuster, qsp pH6 to 7.

3. The moisturizing composition as defined by claim 1, wherein the composition is formulated in a form of emulsion.

4. A regime or regimen for hydrating or moisturizing a skin in need thereof, wherein the regime or regimen comprises topically applying thereon a thus effective amount of the moisturizing composition as defined by claim 1.

5. The regime or regimen as defined by claim 4, wherein the regime or regimen comprises providing hydration as early as 2 hours after application.

6. The regime or regimen as defined by claim 4, wherein said skin in need thereof comprises a mild to moderate dry skin.

7. The regime or regimen as defined by claim 4, wherein said skin in need thereof comprises a dry skin.

8. The regime or regimen as defined by claim 4, wherein said skin in need thereof is a human skin.

9. The moisturizing composition of of claim 1, wherein the composition further comprises a natural moisturizing factor selected from the group consisting of amino acids, ceramides; hyaluronic acid, cholesterol, fatty acids, triglycerides, phospholipids, glycosphingolipids, urea, linoleic acid, glycosaminoglycans, mucopolysaccharide, and a mixture thereof.

10. The moisturizing composition of claim 3, wherein the emulsion is formulated as a cream, a lotion, a gel, an impregnated towel, a patch, a cleansing product, a body wash, or a face wash.

* * * * *